(12) United States Patent
Calabrese

(10) Patent No.: US 11,464,215 B2
(45) Date of Patent: Oct. 11, 2022

(54) MEASUREMENT APPARATUS FOR MEASURING A SPECIFIC GRAVITY OF A LIQUID, AND SALTWATER AQUARIUM SALINITY CONTROL SYSTEM

(71) Applicant: Gerard A. Calabrese, Southwest Ranches, FL (US)

(72) Inventor: Gerard A. Calabrese, Southwest Ranches, FL (US)

( * ) Notice: Subject to any disclaimer, the term of this patent is extended or adjusted under 35 U.S.C. 154(b) by 877 days.

(21) Appl. No.: 16/356,069

(22) Filed: Mar. 18, 2019

(65) Prior Publication Data
US 2020/0077631 A1 Mar. 12, 2020

Related U.S. Application Data

(60) Provisional application No. 62/644,652, filed on Mar. 19, 2018.

(51) Int. Cl.
| | |
|---|---|
| *A01K 63/04* | (2006.01) |
| *G01N 9/18* | (2006.01) |
| *G01N 9/14* | (2006.01) |
| *G01N 9/12* | (2006.01) |
| *G01N 33/18* | (2006.01) |

(52) U.S. Cl.
CPC .............. *A01K 63/047* (2013.01); *G01N 9/12* (2013.01); *G01N 9/14* (2013.01); *G01N 9/18* (2013.01); *G01N 33/1886* (2013.01)

(58) Field of Classification Search
CPC .. G01N 9/18; G01N 9/14; G01N 9/12; G01N 9/16; A01K 63/047
See application file for complete search history.

(56) References Cited

U.S. PATENT DOCUMENTS

| | | | | |
|---|---|---|---|---|
| 3,952,761 | A * | 4/1976 | Friedland | G01N 9/18 137/91 |
| 4,720,998 | A * | 1/1988 | Hogue | G01N 9/12 73/61.41 |
| 5,551,468 | A * | 9/1996 | Lemke | G05D 21/02 137/91 |
| 5,585,786 | A * | 12/1996 | Clark | G01F 23/706 340/623 |
| 10,048,185 | B2 * | 8/2018 | Wright | G01N 9/002 |
| 2009/0056422 | A1 * | 3/2009 | Quinn | B01J 49/85 73/195 |

* cited by examiner

*Primary Examiner* — Paul M. West
(74) *Attorney, Agent, or Firm* — Laurence A. Greenberg; Werner H. Stemer; Ralph E. Locher

(57) ABSTRACT

A specific gravity measurement apparatus has a specific gravity hydrometer that carries a codestrip at the top. A linear optical encoder is disposed to view the codestrip and to output electronic signals that are indicative of a movement of the codestrip relative to said encoder. The movement is indicative of a change in the specific gravity of the liquid, such as a change in a salinity of the aquarium water in which the hydrometer floats. The measurement apparatus may be incorporated into a saltwater aquarium salinity control system where an electronic controller uses the measurement inputs to control a plurality of pumps for selectively adding saltwater or freshwater to the aquarium water in order to control the salinity of the water at a given setpoint level.

8 Claims, 6 Drawing Sheets

MEASUREMENT APPARATUS FOR MEASURING A SPECIFIC GRAVITY OF A LIQUID, AND SALTWATER AQUARIUM SALINITY CONTROL SYSTEM

CROSS-REFERENCE TO RELATED APPLICATION

This application claims the benefit, under 35 U.S.C. § 119(e), of provisional patent application No. 62/644,652, dated Mar. 19, 2018; the prior application is herewith incorporated by reference in its entirety.

BACKGROUND OF THE INVENTION

Field of the Invention

My invention relates to a measurement system for measuring the specific gravity of a liquid. The invention is particularly directed to measuring the salinity of water and, more specifically, of water in a saltwater environment such as a saltwater aquarium.

It is essential in the context of many applications to know the specific gravity of a liquid. For example, it is essential in the context of alcoholic beverage preparation to know the amount of alcohol in solution (e.g., the alcohol content of beer during the brewing process) or, in the context of saltwater aquariums, to know the salinity, i.e., the amount of all salts (primarily sodium chloride) that are dissolved in the water. Salinity is usually indicated in parts per thousand (ppt). Ocean water ranges from approximately 10 ppt to approximately 50 ppt (Red Sea). Saltwater aquarium water should be in the range of 34-36 ppt, but in specific cases it may be in a range of 27-29 or in the low 30s. A salt content of 34-36 ppt, for example, corresponds to a specific gravity between 1.021 and 1.026.

One of the most reliable ways to measure specific gravity of a liquid is a floating hydrometer. The hydrometer measures the specific gravity, or relative density, which is the relationship between the density of the liquid, such as water, and the density of the liquid to be measured. Hydrometers have a weighted bottom, typically bulbous with a weight inside. The bottom is weighted to sink in the liquid and carries a cylindrical stem that projects partly above the liquid level. The cylindrical stem carries a scale from which a measurement is taken.

In the case of aquarium saltwater, the hydrometer floats to a lower level when the salt content decreases and it is lifted when the salt content increases. The measurement itself is typically taken in a sump, which contains aquarium water, i.e., water having the same salinity as the water in the aquarium tank. The sump is separated from the main tank so as to be perfectly "still" and to allow accurate measurements.

There are other devices available to measure the specific gravity of a liquid. For instance, a variety of electronic devices are available to measure the salinity of water. The electronic devices, which use immersible electrodes, a typically very expensive and they are subject to rather frequent malfunction. The electrodes fail frequently and the result is a loss of control. They also require frequent calibration as normal upkeep.

Float hydrometers are calibrated by weight for the specific gravity of the range of its intended use. The calibration never changes. That is, they do not require calibration after the initial calibration.

One drawback of float hydrometers, in general, is the fact that they provide for a visual, mechanical readout. They are not easily integrated into an automated system, where the current salinity is an underlying parameter for effective salinity control. In other words, it would be advantageous to benefit from the accuracy and dependability of the hydrometer and to also provide for full integration in an electronically controlled, automated salinity control system.

SUMMARY OF THE INVENTION

It is accordingly an object of the invention to provide a measurement system for measuring the specific gravity of a liquid which overcomes the above-mentioned and other disadvantages of the heretofore-known devices and methods of this general type and which provides for a reliable measurement system that may be installed as a stand-alone device or may be incorporated into an automated control system. It is a specific object to provide for an improved aquarium salinity measurement system with an automated salinity measurement apparatus.

With the foregoing and other objects in view there is provided, in accordance with the invention, an apparatus for measuring the specific gravity of a liquid, such as an aquarium salinity measurement apparatus or an alcohol content measurement device. The device comprises:

a housing having an interior partly filled with the liquid up to a given fill level;

a specific gravity hydrometer movably disposed in the housing, the specific gravity hydrometer carrying a codestrip;

a linear optical encoder disposed to view the codestrip and configured to output electronic signals indicative of a movement of the codestrip relative to the encoder and indicative of a change in the specific gravity of the liquid.

It is a specific advantage of floating hydrometers that their reaction to a change in the specific gravity is virtually immediate. The corresponding signal change at the output of the electronic system of the invention, therefore, is also virtually immediate. This renders the novel system far superior to conventional specific gravity measurement devices, such as electronic salinity measurement devices.

In accordance with an added feature of the invention, the housing is a tube with an open bottom enabling the hydrometer to be inserted into the tube, the tube having a viewing window formed therein enabling a scale on the hydrometer to be observed inside the tube, and the tube having a water level indicator formed thereon for indicating where the housing is to be mounted relative to a liquid level.

In accordance with an added feature of the invention, there is provided a mounting bracket disposed above a designated water level for mounting the housing to a sidewall of a water sump or to a wall of an aquarium, the mounting bracket being formed with oblong mounting holes for fine adjustment of a mounting position thereof.

In accordance with an added feature of the invention, the linear optical encoder and the codestrip are configured to determine a vertical movement of the hydrometer within a sub-millimeter range. Specifically, the codestrip is formed with horizontal lines at a sub-millimeter spacing, for example, at a vertical spacing of 140 µm between the lines. The codestrip may be mounted (e.g., glued) to the upper tip of a glass hydrometer, it may be inserted inside the tubular stem of a glass hydrometer or it may be directly formed on or printed on the hydrometer stem.

In accordance with an added feature of the invention, there are provided one or more visual indicators for indicating whether or not the salinity level of the aquarium water lies within a setpoint range, or if the salinity lies below the setpoint range or if the salinity lies above the setpoint range. In a preferred embodiment, the visual indicators are LEDs connected to a microcontroller of the optical encoder.

In accordance with a concomitant feature of the invention, a reset switch is connected to a microcontroller of the optical encoder for calibrating the setpoint range. That is, once the apparatus is mounted and the proper salinity of the saltwater has been determined, the user may push/touch the reset switch and the apparatus is calibrated to its baseline setpoint. Any downward or upward movement of the hydrometer can now be interpreted as a departure from the setpoint (i.e., an increase or a decrease in the salinity).

With the above and other objects in view there is also provided, in accordance with the invention, a saltwater aquarium salinity control system, comprising:

an aquarium salinity measurement apparatus as outlined above;

an electronic controller having an input connected to receive an output from said measurement apparatus, the output carrying information regarding a salinity of an aquarium water;

a plurality of pumps connected to said electronic controller for selectively adding saltwater or freshwater to the aquarium water in dependence on a measurement received by said electronic controller from the measurement apparatus.

Other features which are considered as characteristic for the invention are set forth in the appended claims.

Although the invention is illustrated and described herein as embodied in an apparatus for measuring the specific gravity of a liquid and to an aquarium salinity measurement system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
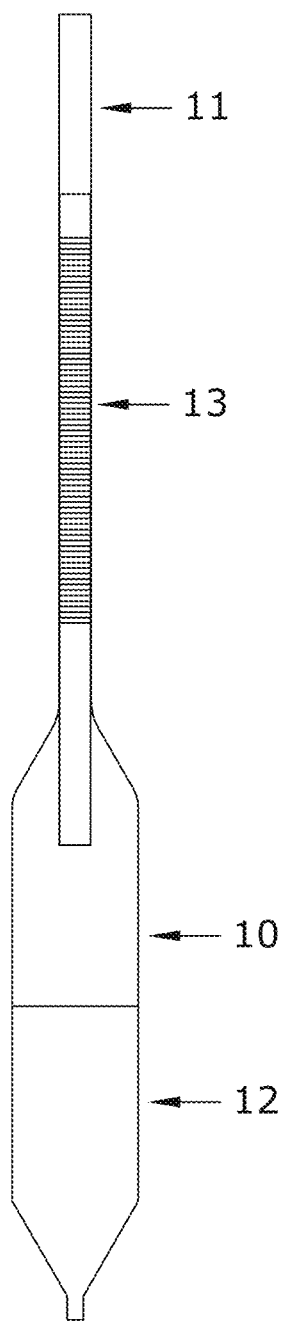
FIG. 1 is a side elevation view of an exemplary specific gravity hydrometer according to the prior art.

The instant invention provides for a salinity measurement system that provides for a fully automatic measurement and for a fully automatic electronic output. Further, the device provides for a very accurate measurement. The description of an exemplary embodiment below will be directed to an aquarium water salinity measuring apparatus. The invention, however, is not limited to the specific implementation. The apparatus is suitable, more generally, to any measurement of the specific gravity of a liquid.

With regard to the drawing figures below, it should be noted that the measurements (in millimeters, mm) are provided by way of example only. The dimensions may be varied within a very large range. Also, the ratios of width, length and depth may be varied within a great range. The dimensions are illustrated to scale only with regard to the exemplary embodiment.

Referring now to the figures of the drawing in detail and first, particularly, to FIG. 1 thereof, there is shown a prior art specific gravity float hydrometer. The main body is a sealed hollow glass tube with a bulbous bottom portion 10 and a stem portion 11. A ballast 12 is integrated in the bulbous bottom portion 10. Since most float hydrometers are used in sanitary context (e.g., food preparation, chemical laboratories), the ballast 12 is made from non-toxic and/or non-heavy metal containing materials. The stem portion 11 of the device is provided with at least one measurement scale 13 formed with graduations.

The float hydrometer is based on the buoyancy principle, namely, the force pushing the device upward (buoyant force) equals the weight of the liquid that is displaced by the submerged portion of the device. The heavier the displaced volume, the stronger the upward force. That is, the hydrometer will sink lower in liquids with a low density and it will rise higher in liquids with a high density. In the context of salinity measurement, freshwater has a lower density than saltwater because salt ions are heavier than water molecules. The higher the salinity, i.e., the salt content in the water, the denser the water and the higher the hydrometer will float.

Figure 2:
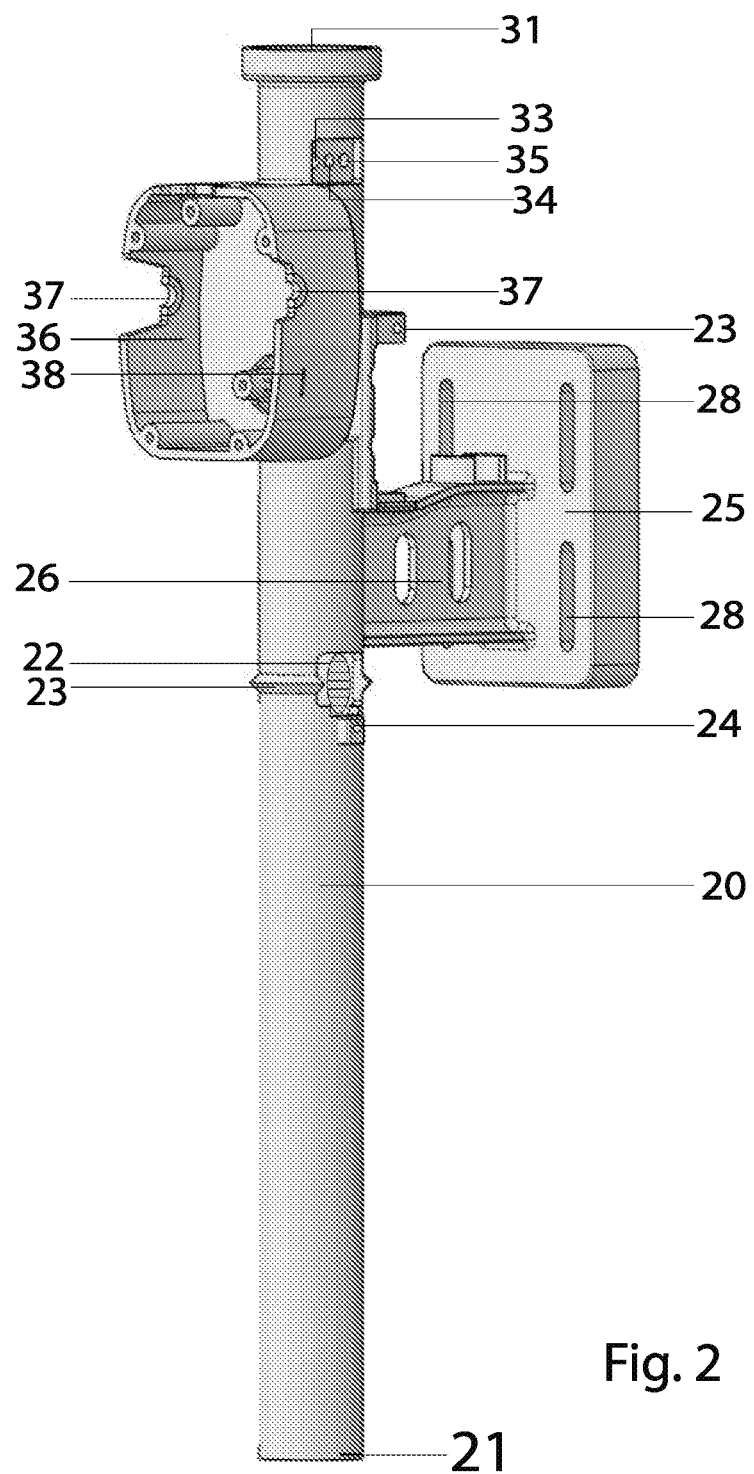
FIG. 2 is a perspective of a hydrometer assembly according to the invention.
Figure 3:
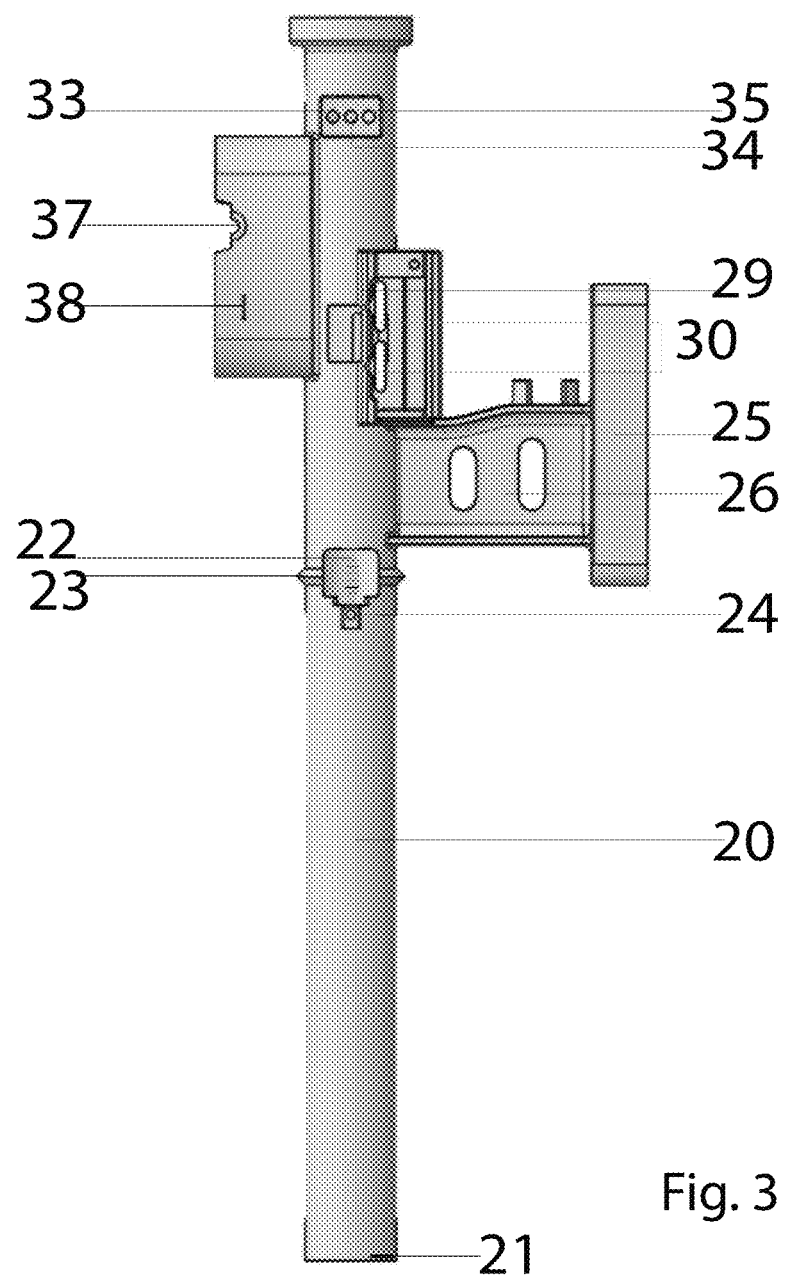
FIG. 3 is a side elevation view thereof.
Figure 4:
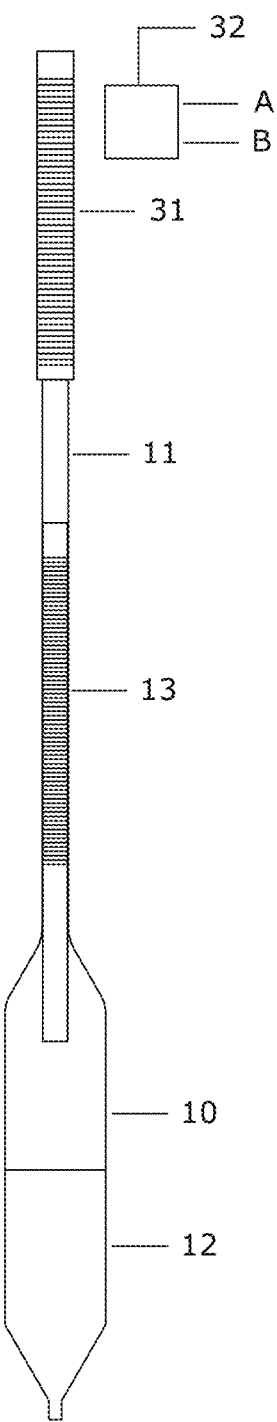
FIG. 4 is a side elevation of a specific gravity hydrometer carrying a codestrip, and illustrating an associated optical encoder.

Referring now to FIG. 2, the hydrometer floats inside a main tube 20, which forms the hydrometer outer body. The diameter of the tube is selected so as to allow the hydrometer to freely move up and down within the tube 20. Also, the tube 20 is formed to have no obstacle to the free movement of the hydrometer when the same is installed in a vertical position. The main tube 20 is open at the bottom so that water may freely enter into the tube and also freely exchange with surrounding water. After the hydrometer is inserted into the tube, there may be provided a small locking tab 21 at the bottom mouth of the tube to prevent the hydrometer from slipping out.

The device is mounted on the sidewall of the sump or the actual aquarium tank so as to be immersed to the indicated water line. It is important that the water level at the hydrometer be still so that accurate and dependable readings may be had. That is, whether the device is mounted in a sump or in the aquarium itself, it must be protected against level fluctuations. This may be achieved by baffles or even by proper intermediate tubing.

The tube 20 is typically made of opaque material. The actual reading of the hydrometer may be observed through a small viewing window 22 formed in the tube 20. The hydrometer scale 13 is shown in the viewing window 22. The proper mounting height is indicated by a ridge indicator 23 formed on the outside of the tube 20. There is also provided a hydrometer stabilizing clip, which causes the hydrometer to remain centered inside the tube, yet provides for easy and unimpeded vertical movement. A support mount screw hole 24 is provided for that purpose.

The tube 20 and the other elements of the device are mounted by way of a mounting bracket 25. The level of the device may be adjusted by attaching and moving an attachment bracket 25 up or down. For that purpose, the mounting bracket 25, which is connected to the main tube 20 by way of a bridge 26, is formed with oblong mounting holes 28. Further there is a fine adjustment screw provided to finely adjust the placement after the initial setting is made.

The sensor is an optical encoder that is disposed to measure the movement of a codestrip 31 attached at the top of the hydrometer. The optical encoder 32 is placed in a housing 29. An optical encoder mount 30 provides for fine adjustment so that the height of the encoder may be accurately adjusted.

The codestrip 31 has spaced gradations that are "visible" to the sensor of the optical encoder 32. By way of example, the codestrip 31 carries horizontal lines that are spaced from one another at 140 µm. As the hydrometer moves, the encoder 32 senses the movement of the code strip 31 and produces two signals A, B that are interpreted by the micro controller. That is, the sensing unit is comprised of an optical encoder that tracks the hydrometer movement up or down and relays this information to the central controller.

The optical encoder 32, here a digital linear optical encoder, is an active device that has two outputs (channels A & B) and consists of a lensed LED source and a detector IC. Each of the two outputs of the digital device emit a square wave pulse. The two signals A, B are 90 degrees out of phase. Depending on the code strip motion, whether it moves up or down, channel A leads or lags channel B. That is, depending on which of the channels leads or lags, the microcontroller is able to determine the direction of movement of the code strip. After the initial calibration to the baseline, the device is able to accurately determine the movement up or down of the floating hydrometer and also determine the amount of movement. The amount of movement, i.e., the displacement distance, is determined by counting the number of gradations (i.e., horizontal lines) on the passing code strip. In the exemplary embodiment, a count of 10 would indicate a movement of 1.4 mm (10×140 µm).

By way of example, I have incorporated an optical encoder HEDS-974X, available from Broadcom. The typical current draw of the device is approx. 20 milliamperes and the typical supply voltage is 5V.

From the output signals of the code strip sensor, the microcontroller determines whether the hydrometer moves up or down. The microcontroller is programmed to read the sensor signals and to determine the direction of the movement of the codestrip, and thus of the hydrometer. In the instant system, a quadrature decoder is most advantageous. The system samples the A and B signals at the sample time, and thus forms an "image" of a current state. This image is compared to the last-sampled image. If the two are identical, no movement has been detected. If, say, A has changed but B has not, and A is the leading signal, the controller determines that a single increment in the forward (e.g., up) direction has occurred. If, say, B has changed and A has not, the controller determines that the device has moved in the opposite (e.g., down) direction. Both signals will not change during a single sampling period.

Depending on the spacing of the codestrips on the hydrometer scale, the sensor may detect motion within a very small range, namely, down to a hydrometer motion as low as a few microns. Assuming a spacing, as on the exemplary codestrip, of 140 microns, the system can easily and safely determine movements in the micron range. In either case, the measurement resolution lies in the sub-millimeter range.

The microcontroller is disposed in a microcontroller housing 36. Connections to the controller through an opening 37 for a cable to connect the microcontroller to a relay board. There is also provided an opening 38 for a cable that connects the optical encoder with the microcontroller.

The initial calibration is effected by the user setting the setpoint salinity level. This may be done by momentarily pressing a capacitive touch button 31 located at the top of the tube 20. The green LED 34 should turn on, indicating a good salinity level. Any changes to the salinity level will cause the hydrometer to move up or down. If the salinity rises beyond a preset amount, the red LED 33 will turn on. If the salinity undershoots the preset level the amber/yellow LED 35 turns on. It will be understood that the indicator may be implemented in a single LED, which is capable of electively turning green, red, or amber/yellow.

The user may acquire a current salinity level reading through the viewing window 22, which exposes the scale 13 on the hydrometer. Since the latter is permanently calibrated the user may rely on the reading of the scale 13 before pushing the calibration button 31.

Instead of three indications—green, red, yellow—there may also be provided a digital output, preferably numerical. Since the optical encoder provides measurement output in the sub-micron range, the corresponding salinity measurement is also available at a high resolution. There may, therefore, be provided a digital display showing the salinity at one or even two decimal positions.

It is, furthermore, also possible to use the output signals of the microcontroller in a more sophisticated system. For instance, the output signals may be used in an automated salinity control apparatus as described in my U.S. Pat. No. 10,070,628 B2. There, the salinity sensor measures the salinity in a salt-mixed reservoir, which is used to supply the aquarium with properly balanced salt water. When the sensor indicates a salinity value that is too low, fully salt-saturated water is added into the salt-mixed reservoir. If the sensor indicates a salinity value that is too high, deionized water is supplied into the salt-mixed reservoir. In this way, the salinity of the water is maintained at a proper level.

Figure 5:
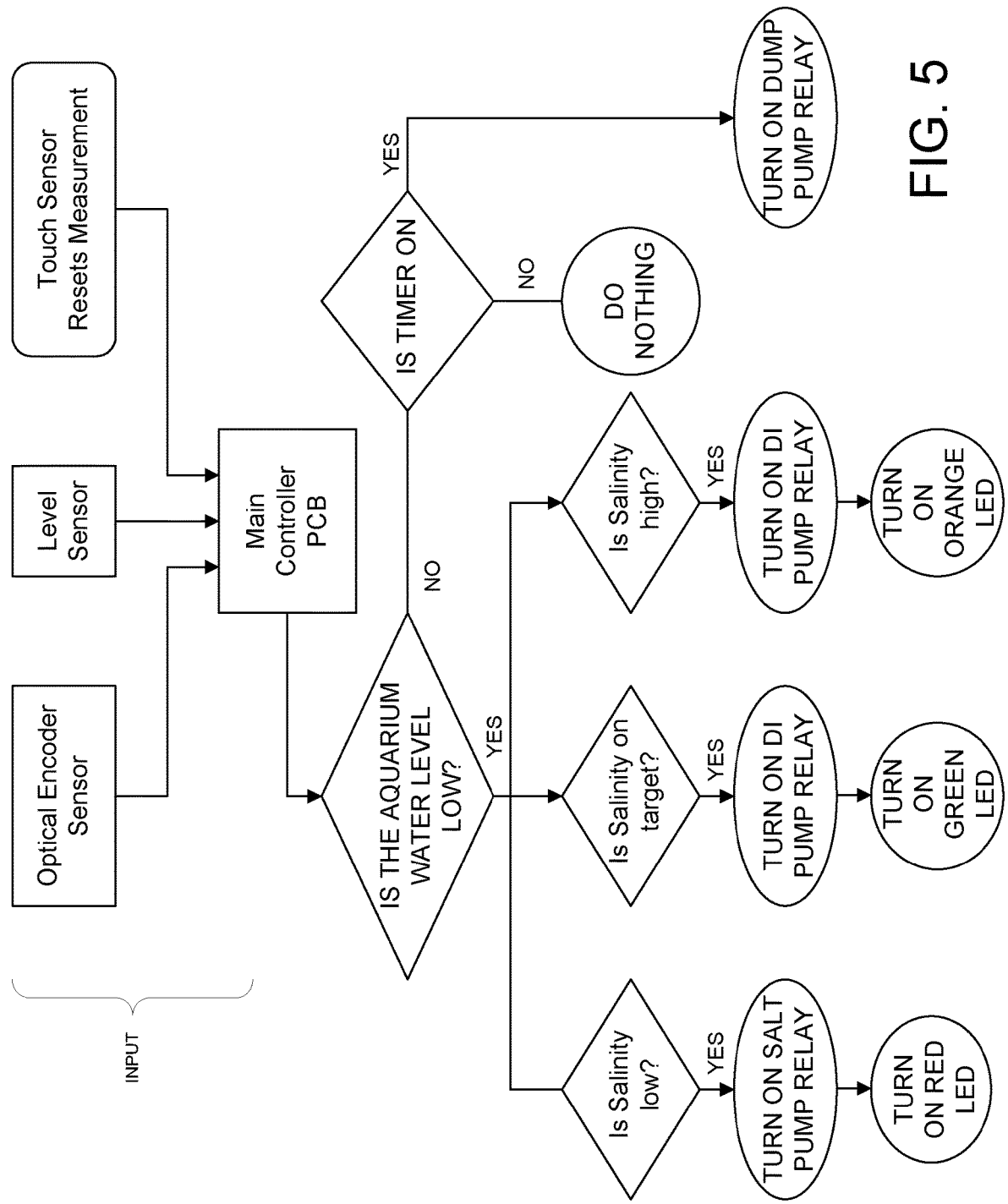
FIG. 5 is a flowchart illustrating a control program of an saltwater aquarium salinity controller.

The integration into the salinity control system of U.S. Pat. No. 10,070,628 B2 is illustrated in FIG. 5. The main controller of the system receives inputs from a level sensor, from a calibration sensor that resets the measurement, and from the optical encoder. After querying whether or not the aquarium water level is sufficient, the system continues with checking on the salinity level. If the salinity is low, the system adds salt into the water. If the salinity is high, the system adds de-ionized water into the aquarium. If the salinity is at the proper level, the system adds de-ionized water until the salinity measurement indicated a low salinity level, whereupon the salt pump relay is turned on. That is, the system cycles between DI water and salt water in order to properly fill the tank and to maintain a proper salinity.

Figure 6:
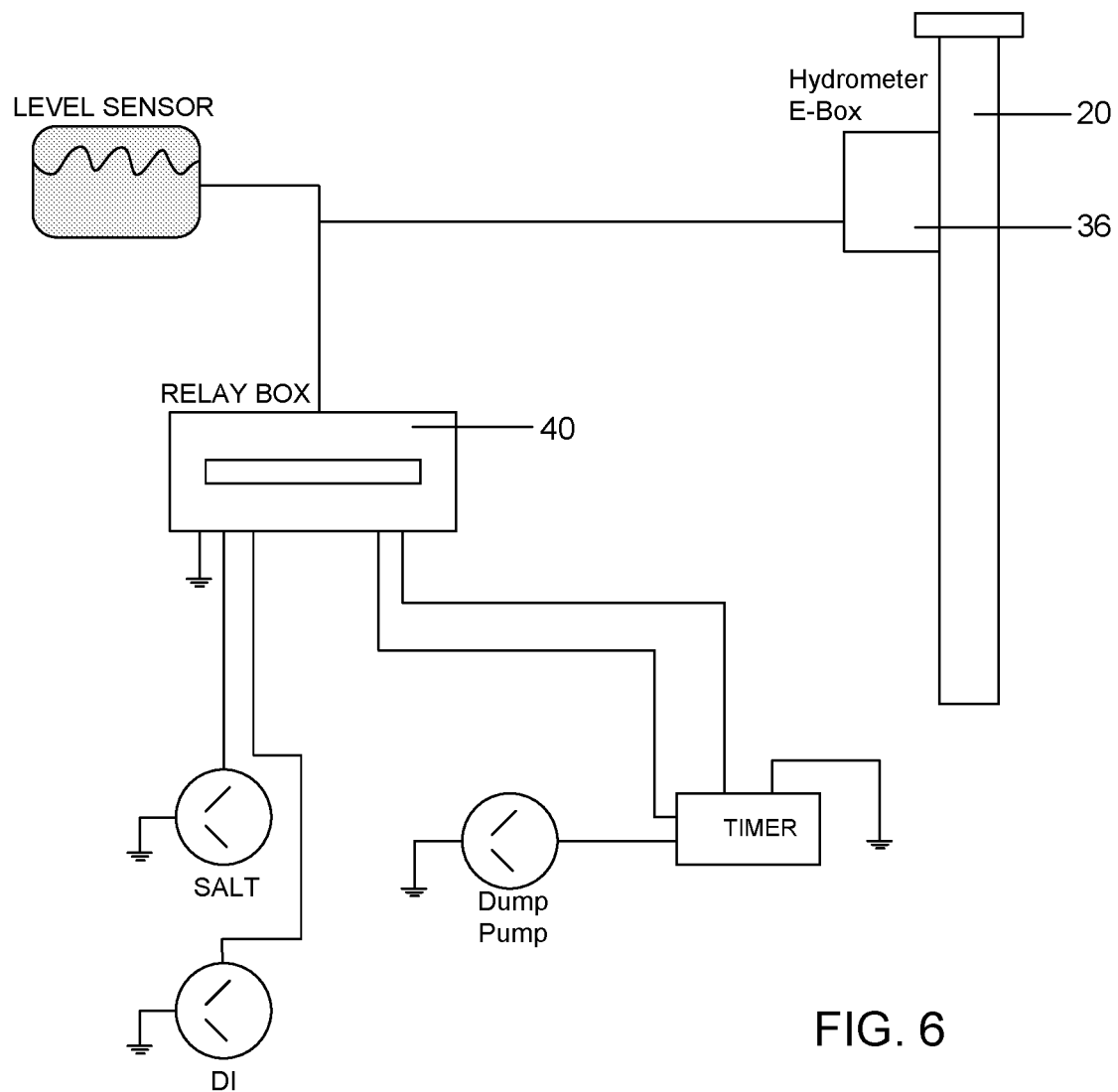
FIG. 6 is a schematic view of a salinity control system with an integrated hydrometer according to the invention.

An overall schematic system view is illustrated by way of the schematic in FIG. 6. There, the output signal of the optical encoder indicating whether the salinity is within the setpoint range or it is low or high, is fed to a main aquarium controller, or simply a relay box 40. The controller 40, which forms a logic brain of the salinity control system, controls the peristaltic pumps accordingly. Information regarding the control is found in my earlier patent U.S. Pat. No. 10,070,628 B2, which is herewith incorporated by reference.

The invention claimed is:

1. An apparatus for measuring a specific gravity of a liquid, the apparatus comprising:

a housing having an interior to be partly filled with the liquid up to a given fill level;

said housing including a mounting bracket disposed above a designated water level for mounting said housing to a sidewall of a water sump or to a wall of an aquarium, said mounting bracket being formed with oblong mounting holes for fine adjustment of a mounting position thereof;

a specific gravity hydrometer movably disposed in said housing, said specific gravity hydrometer carrying a codestrip;

a linear optical encoder disposed to view said codestrip and configured to output electronic signals indicative of a movement of said codestrip relative to said encoder and indicative of a change in the specific gravity of the liquid.

2. The apparatus according to claim 1, wherein said housing is a tube with an open bottom enabling said hydrometer to be inserted into said tube, said tube having a viewing window formed therein enabling a scale on said hydrometer to be observed inside said tube, and said tube having a liquid level indicator formed thereon for indicating where said housing is to be mounted relative to a liquid level.

3. The apparatus according to claim 1, wherein said specific gravity hydrometer is calibrated for an aquarium water salinity measurement.

4. The apparatus according to claim 1, wherein said linear optical encoder and said codestrip are configured to determine a vertical movement of said hydrometer within a sub-millimeter range.

5. The apparatus according to claim 1, which further comprises one or more visual indicators for indicating whether or not the salinity level of the aquarium water lies within a setpoint range, or if the salinity lies below the setpoint range or if the salinity lies above the setpoint range.

6. The apparatus according to claim 5, wherein said visual indicators are LEDs connected to a microcontroller of said optical encoder.

7. The apparatus according to claim 5, which further comprises a reset switch connected to a microcontroller of said optical encoder for calibrating the setpoint range.

8. A saltwater aquarium salinity control system, comprising:

an apparatus according to claim 1 calibrated for aquarium water salinity measurements;

an electronic controller having an input connected to receive an output from said measurement apparatus, the output carrying information regarding a salinity of the aquarium water;

a plurality of pumps connected to said electronic controller for selectively adding saltwater or freshwater to the aquarium water in dependence on a measurement received by said electronic controller from said measurement apparatus.

* * * * *